United States Patent [19]

Cambio, Jr.

[11] Patent Number: 4,967,741
[45] Date of Patent: Nov. 6, 1990

[54] RETAINING DEVICE

[75] Inventor: Orlando D. Cambio, Jr., Bristol, Wis.

[73] Assignee: Hudson Respiratory Care Inc., Temecula, Calif.

[21] Appl. No.: 282,080

[22] Filed: Dec. 9, 1988

Related U.S. Application Data

[63] Continuation of Ser. No. 170,956, Mar. 21, 1988, abandoned, which is a continuation of Ser. No. 921,178, Oct. 21, 1986, abandoned, which is a continuation of Ser. No. 747,218, Jun. 21, 1985, abandoned.

[51] Int. Cl.$^5$ .............................................. A61M 15/00
[52] U.S. Cl. .................................. 128/200.11; 604/43; 285/114
[58] Field of Search ............... 128/207.14, 207.15, 128/207.17, DIG. 26, 201.11, 20.13, 20; 604/93, 283, 905, 403–411; 285/61, 114; 248/225.31, 231.8, 302; D24/51–54, 56, 58

[56] References Cited

U.S. PATENT DOCUMENTS

| | | | |
|---|---|---|---|
| 3,746,000 | 7/1973 | Edwards | 128/200.11 |
| 3,804,280 | 4/1974 | van Ameronger et al. | 128/200.11 |
| 3,991,912 | 11/1976 | Soto | 604/202 |
| 4,082,094 | 4/1978 | Dailey | 604/93 |
| 4,230,109 | 10/1980 | Geiss | 604/93 |

Primary Examiner—Randall L. Green
Assistant Examiner—K. M. Reichle
Attorney, Agent, or Firm—Powell L. Sprunger

[57] ABSTRACT

A retaining device comprising, a reservoir for retaining a liquid, a first elongated conduit, and a second elongated conduit. An upper end of the first and second conduits is connected in fluid communication to the reservoir. Upper ends of the first and second conduits are retained to the reservoir in order to prevent them from inadvertently pulling out from the reservoir.

12 Claims, 2 Drawing Sheets

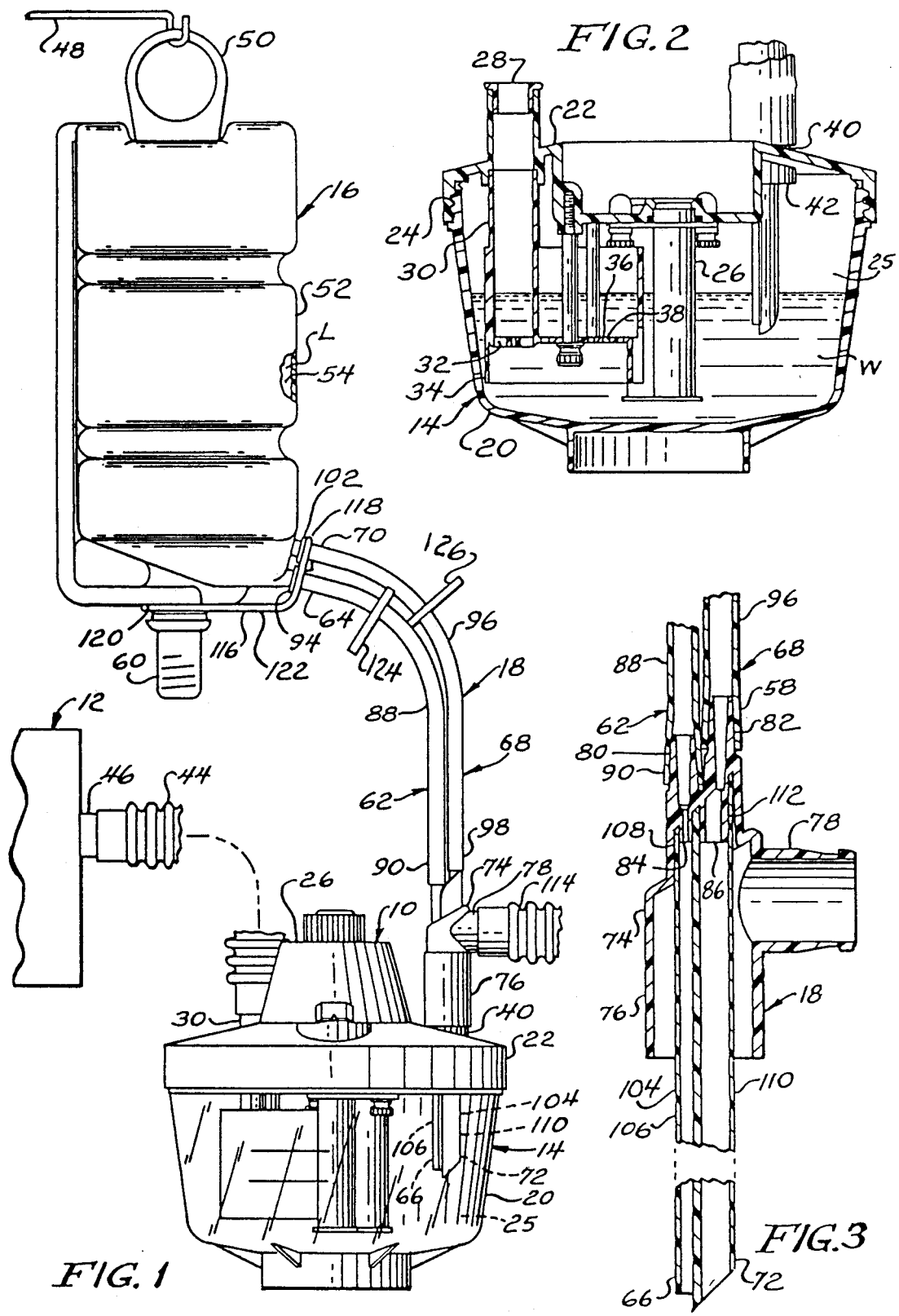

RETAINING DEVICE

This is a continuation of application Ser. No. 170,956, filed Mar. 21, 1988, which is a continuation of Ser. No. 921,178, filed Oct. 21, 1986, which is a continuation of Ser. No. 747,218, filed June 21, 1985, all now abandoned.

BACKGROUND OF THE INVENTION

The present invention relates to retaining devices.

Humidifiers in a breathing circuit for a patient are known. In such systems, a sterile liquid is placed in the humidifier with the liquid being heated, and an air mixture is passed from a ventilator through the liquid in order to heat and humidify the air mixture, and the resulting air mixture is passed to the patient.

It is contemplated to automatically refill the humidifier from a liquid retaining reservoir by a double lumen tube which is connected between the reservoir and the humidifier. However, if one of the tubes should inadvertently become detached from the reservoir, the liquid from the reservoir may rapidly pass through the other tube into the humidifier, and the vantilator may pump the excess liquid from the humidifier to the patient which could result in drowning of the patient. Of course, it is desirable to prevent this result.

SUMMARY OF THE INVENTION

A principal feature of the present invention is the provision of a retaining device for a humidifying system.

The device comprises a reservoir for retaining a liquid, first elongated conduit means, and second elongated conduit means. The device has means for connecting an upper end of the first and second conduit means in fluid communication to the reservoir.

A feature of the present invention is the provision of means for retaining upper ends of the first and second conduit means to the reservoir.

Another feature of the present invention is that the retaining means prevents the upper ends of the conduit means from inadvertently pulling out from the reservoir.

Yet another feature of the invention is that the retaining means prevents rapid passage of liquid through one of the conduit means into a humidifying system with possible deleterious results to a patient.

Further features will become more fully apparent in the following description of the embodiments of this invention and from the appended claims.

DESCRIPTION OF THE DRAWINGS

In the drawings:

FIG. 1 is a fragmentary plan view of a humidifying system of the present invention;

FIG. 2 is a sectional view of a humidifier for the system of FIG. 1;

FIG. 3 is a fragmentary sectional view of a feeding system for the system of FIG. 1;

DESCRIPTION OF THE PREFERRED EMBODIMENTS

Figure 4:
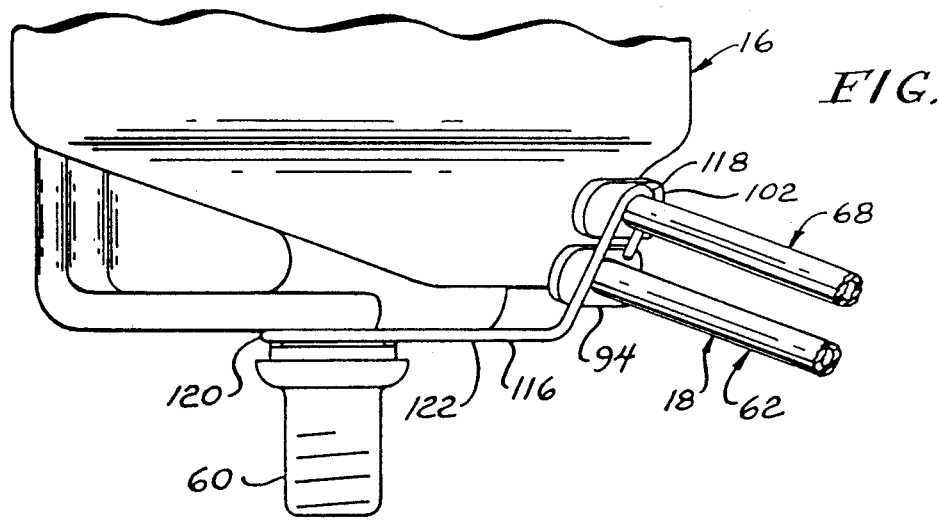
FIG. 4 is a fragmentary perspective view of a lower portion of a reservoir for the system of FIG. 1.

Referring now to FIGS. 1-3, there is shown a humidifying system generally designated 10 comprising a ventilator 12 of known type, a humidifier 14 of known type, a reservoir 16 for retaining sterile water, and a feeding system 18 according to the present invention.

As shown, the humidifier 14 has a bowl 20 to retain a supply of sterile water W in a lower part thereof, and a lid 22 releasably attached to an upper part of the bowl 20 by suitable means such as threads 24, with the bowl 20 and lid 22 defining a chamber 25. The humidifier 14 also has a heater 26 of known type in order to heat the water W in the humidifier 14. The humidifier 14 has an inlet port 28 of an elongated tubular section 30 with a lower part of the tubular section 30 located beneath the level of the water W, and with the lower part of the tubular section 30 having apertures 32 to permit passage of gas therethrough. The humidifier 14 has an annular flange 34 extending from a side of the tubular section 30 toward a central portion of the bowl 20, with an upper wall or sparger plate 36 being located alongside the tubular section 30 above the annular flange 34 and having a plurality of relatively small apertures 38 for a purpose which will be described below. As shown, the sparger plate 36 is located beneath the level of the water W. The humidifier 14 also has a tubular section 40 on the lid 22 defining an outlet port 42.

The system 10 has a corrugated tube 44 connected to an outlet 46 of the ventilator 12 to the inlet port 28 of the humidifier 14. In use, the ventilator 12 delivers a volume of gas, such as an oxygen mixture, in cycles with the pressure and volume being controlled in order to simulate the normal breathing mechanism of a patient. The gas is delivered through the tube 44 and tubular section 30 into the water W through the apertures 32 to a location intermediate the flange 34. The gas then passes through the apertures 38 of the sparger plate 36 and through the water to a location above the level of the water W. The sparger plate 36 provides improved mixing of the gas with the water, and breaks up the gas flow to avoid large bubbles. As the gas passes through the water W and the sparger plate 36 it is humidified by the water W. Also, the heater 26 heats the water W, and the heated water in turn heats the gas while passing through the water W. The heated and humidified gas passes along the surface of the water W and through the outlet port 42 to the patient, as will be further described below.

Figure 6:
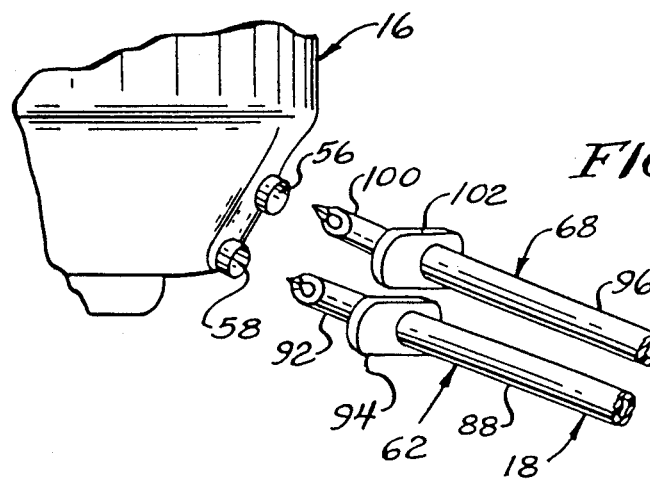
FIG. 6 is a perspective view illustrating upper ends of conduits for placement in a lower part of the reservoir.

The reservoir 16 is suspended by suitable means, such as a hook 48, received in an upper ring 50 of the reservoir 16 at a location above the humidifier 14. The reservoir 16 has an outer wall 52 defining a chamber 54 to retain sterile water or liquid L which is fed to the humidifier 14, as will be described below. With reference to FIGS. 4 and 6, the reservoir 16 has a pair of lower openings 56 and 58, and a downwardly extending protuberance 60 adjacent the openings 56 and 58.

With reference to FIGS. 3 and 6, the feeding system 18 of the present invention has a first water conduit means 62 having an upper end 64 connected to the reservoir 16, and a lower end 66 received in the humidifier 14. The feeding system 18 also has a second gas conduit means 68 having an upper end 70 connected to the reservoir 16, and and a lower end 72 received in the humidifier 14. The feeding system 18 has an elbow 74 having a hollow first cylindrical part 76 extending around and spaced from the first and second conduit means 62 and 68, and a hollow cylindrical second part 78 communicating with the first part 76 and extending at approximately a 90 degree angle to the longitudinal axes of the first and second conduit means 62 and 68. The elbow 74 has first and second upwardly directed hollow nipples 80 and 82, and third and fourth downwardly directed hollow nipples 84 and 86, with the first nipple 80 communicating with the third nipple 84 and with the second nipple 82 communicating with the fourth nipple 86. As shown, the nipples 80-86 are located above the first and second parts 76 and 78 of the elbow 74.

The first conduit means 62 has an upper tubular section 88 with a lower end 90 received on the first nipple 80. The tubular section 88 has an upper end terminating in a spike 92 for connecting the tubular section 88 in fluid communication to the reservoir 16 through the opening 58. The tubular section 88 also has an outwardly directed flange 94 adjacent the spike 92 to limit movement of the tubular section 88 into the reservoir 16. The second conduit means 68 has an upper tubular section 96 having a lower end 98 connected to the second nipple 82. The tubular section 96 has a hollow spike 100 for connecting the second conduit means 68 to the reservoir 16 through the opening 56. The tubular section 96 has an outwardly directed flange 102 adjacent the spike 100 to limit movement of the spike 100 into the reservoir 16.

As shown in FIG. 3, the lower ends of the first and second conduit means 62 and 68 are defined by a coextruded double lumen tubular section 104 having a first tube 106 of the first conduit means 62 with an upper end 108 received on the third nipple 84, and a second tube 110 of the second conduit means 68 having an upper end 112 received on the fourth nipple 86. In use of the system 10, the first part 76 of the elbow 74 is attached to the tubular section 40 of the humidifier 14, and in this configuration, the tubular section 104 extends through the first part 76 of the elbow 74 to a location substantially below the elbow 74 into the bowl 20 of the humidifier 14.

As shown in FIG. 3, the outside diameter of the first tube 106 is substantially smaller than the outside diameter of the second tube 110, with the inside diameter of the first tube 106 being made as small as possible, and the inside diameter of the second tube 110 being made as large as possible for purposes which will be described below. In a preferred form, the internal diameter of the first tube 106 is approximately 0.080 inches in diameter, the internal diameter of the second tube is approximately 0.760 inches in diameter, and the internal diameter of the first part 76 of the elbow 74 is approximately 0.730 inches in diameter which is greater than the width of the tubular section 104 which is approximately 0.470 inches. Also the lower end 72 of the second conduit means 68 is formed at an angle of approximately 45 degrees to the longitudinal axis of the second conduit means 68 for a purpose which will be describe below. The lower end of the first conduit means 62 is formed at an angle of approximately 90 degrees to the longitudinal axis of the first conduit means 62. As shown, the lowermost portion of the angle formed part of the lower end 72 of the second conduit 68 is located adjacent the lower end 66 of the first conduit means 62, and the lower end 66 of the first conduit means 62 is preferably located intermediate the lower and upper portions of the angle formed part of the second conduit means 68.

In a further description of the use of the system 10, with reference to FIGS. 1-3, a corrugated tube 114 is connected to the second part 78 of the elbow 74 and extends to the patient When the first part 76 of the elbow 74 is connected to the tubular section 40 of the humidifier 14, the heated humidified gas passes through the outlet port 42, the first and second parts 76 and 78 of the elbow 74 and through the tube 114 to the patient for therapy.

Figure 5:
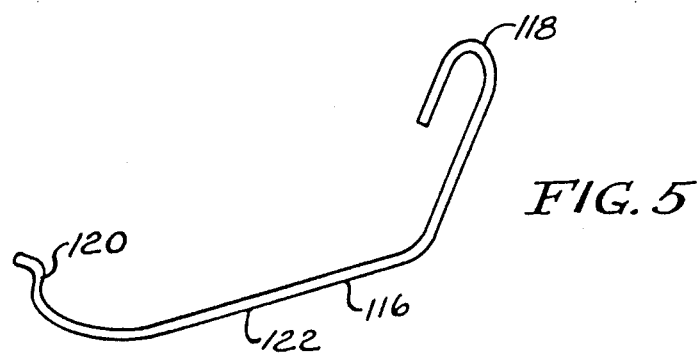
FIG. 5 is a perspective view of a clip for the reservoir of FIG. 4.

With reference to FIGS. 4 and 5, the system 10 has a clip 116 to retain the first and second conduit means 62 and 68 to the reservoir 16. The clip 116 has a first hook portion 118 at one end of the clip 116 received on the first and second conduit means 62 and 68 adjacent the flanges 94 and 102. The clip 116 has a second hook portion 120 at the other end of the clip 116 extending partially around the protuberance 60 of the reservoir 16. The clip 116 has a central portion 122 connecting the first and second hook portions 118 and 120. The first hook portion 118 may first be secured about the first and second conduit means 62 and 68, and the second hook portion 120 may then be secured about the protuberance 60 of the reservoir 16. In this manner, the clip 116 retains the first and second conduit means 62 and 68 in the reservoir 16 to prevent accidental pulling out of the first and second conduit means 62 and 68 for a purpose which will be described below. The clip 116 may be made of any suitable material, such as metal.

During use of the system 10, the water W which is utilized to humidify the gas which passes to the patient reduces the water level in the bowl 20 of the humidifier 14 and, in the past, it was necessary to periodically replenish the supply of water W in the humidifier 14. The procedure would normally be carried out by removing the lid 22 from the bowl 20, and pouring water into the bowl 20 to raise the level of water in the bowl 20. It has been found that this procedure is inconvenient, and also poses the possibility of contamination to the water which is poured into the bowl 20 during handling. Other procedures are to pour water through one of the ports of a cap for the humidifier. Alternatively, water can be fed from a suspended flexible solution bag through a special set. The disposable set which is manufactured by a company consists of a tee adapter which fits over the cascade outlet. The patient hose is connected to the perpendicular leg of the tee and the remaining leg is connected to the solution bag via a vinyl tube. Water is delivered through the adapter to the cascade by opening a tube clamp when required. Although the filling process is simplified it is still manual requiring frequent attention. Further versions of the humidifier offer a special port for inserting a water feed system. The system, manufactured by a company, is composed of a suspended glass bottle which feeds the water through a large bore tube to a valve assembly which is positioned within the cannister. The valve is automatically closed when the water level reaches the required height. Although the system continuously feeds water as needed, the set-up must be cleaned and sterilized for re-use.

In accordance with the present invention, the feeding system 18 automatically feeds water from the reservoir 16 to the bowl 20 of the humidifier 14 in order to maintain the desired level of water W in the humidifier 14. When the level of water W is below the lower end 72 of the second conduit means 68, gas passes through the second conduit means 68 and bubbles up through the liquid L in the reservoir 16, while water passes downwardly through the first conduit means 62 into the humidifier 14. However, when the water rises in the humidifier 14 and closes off the second conduit means 68, the water continues flowing for a time from the reservoir 16 through the first conduit means 62 into the humidifier 14, and develops a vacuum above the head of liquid L in the reservoir 16. In order for the liquid to stop flowing downwardly from the reservoir 16, it is necessary for the vacuum in the reservoir to reach a negative pressure equal to the hydrostatic head in which case the system is at equilibrium. Meanwhile, the water in the humidifier 14 has closed off the second conduit means 68, and water starts rising in the second conduit means 68. The second conduit means 68 fills with water and the system reaches equilibrium.

During further use of the system 10, water is utilized to humidify the gas passing to the patient, and the water level eventually drops below the lower end 72 of the second conduit means 68. At this time, surface tension initially prevents gas from passing up the second conduit means 68, but angle formed downstream end 72 of the second conduit means 68 breaks the surface tension in order to drain the second tube 110 of the second conduit means 68. After the second tube 110 has drained, there exists a greater pressure acting on the lower part of the remaining column of water in the second conduit means 68 than its hydrostatic head, such that the water flows into the reservoir 16, after which normal flow of water begins again through the first conduit means 62, and gas passes upwardly through the second conduit means 68.

In accordance with the present invention, the first tube 106 is made as small as possible in diameter, and the second tube 110 is made as large as possible in diameter while minimizing restriction of gas flow through the elbow 74 to the patient. The first and second tubes 106 and 110 are made of the desired sizes while permitting water feeding of the system 18 from the reservoir 16 to the humidifier 14.

As shown in FIG. 1, the system 18 has a pair of clamps 124 and 126 which may be utilized before the initial filling of the humidifier 14, and while changing reservoirs 16 to close off the first and second conduit means 62 and 68. Of course, the clamps 124 and 126 are open during use of the system to permit passage of liquid and gas through the first and second conduit means 62 and 68.

It is desirable to use the feeding system 18 in connection with the reservoir 16 to initially fill the humidifier 14 to the desired level. If the humidifier 14 was filled through the relatively small first conduit means 62, it would require an extended period of time, such as twenty-five minutes, to reach the desired liquid level in the humidifier 14. Thus, it is desirable to initially fill the humidifier 14 through the relatively large second conduit means 68, and the liquid exits at the lower edge of the formed lower end 72 of the second conduit means 68, while gas passes through the first conduit means 62. However, if the lower ends of the first and second conduit means 62 and 68 were on a straight slant, the water exiting from the second conduit means 68 would be pulled up into the first conduit means 62 which would slow down and possibly stop filling of the humidifier 14 since gas would not be passing up through the first conduit means 62. Hence, in accordance with the present invention, the first conduit means 62 has its lower end 66 spaced slightly above the lowermost part of the formed lower end 72 of the second conduit means 68 to prevent water from passing up into the first conduit means 62 which is being utilized as a gas tube during initial filling of the humidifier 14.

As previously discussed, with reference to FIGS. 4-6, the clip 116 engages against the flanges 94 and 102 of the first and second conduit means 62 and 68 and prevents the first and second conduit means 62 and 68 from pulling out of the reservoir 16. In the event that one of the conduit means 62 or 68 would inadvertently become detached from the reservoir 16 during use of the system 10, there would be a massive leakage of air into the reservoir 16 and passage of liquid out through the exposed associated opening 58 or 56. Also, there would be a continuous stream of water through the remaining connected conduit means 62 or 68 into the humidifier 14, and the ventilator 12 could pump part of tee overfilled water in the humidifier 14 through the tube 114 into the lungs of the patient, which might result in drowning of the patient or other harmful results. Thus, the clip 116 prevents harm to the patient in the event that one of the conduit means 62 and 68 should otherwise become detached from the reservoir 16.

The foregoing detailed description is given for clearness of understanding only, and no unnecessary limitations should be understood therefrom, as modifications will be obvious to those skilled in the art.

I claim:

1. A retaining device, comprising:
   a reservoir for retaining a liquid having a wall defining openings;
   a humidifier;
   first elongated conduit means having an upper end and a lower end;
   second elongated conduit means having an upper end and a lower end, the upper ends of the first and second conduit means being removably connected to the openings of the reservoir;
   means for connecting the lower end of the first and second conduit means in fluid communication to the humidifier; and
   means for retaining the upper ends of the first and second conduit means to the reservoir to prevent them from inadvertant removal from the reservoir, wherein the upper ends of the first and second conduit means have an outwardly directed flange, wherein the reservoir has an outwardly directed protuberance spaced from the openings, and in which the retaining means comprises means for clipping the flanges to the protuberance.

2. The device of claim 1 further comprising a pair of hollow spikes at the upper end of the first and second conduit means, respectively, and removably received through the openings of the wall of the reservoir, said spikes being in fluid communication with the respective conduit means and the reservoir.

3. A retaining device, comprising:
   a reservoir for retaining a liquid and having a pair of lower openings and an outwardly directed protuberance adjacent the openings;
   first elongated conduit means having an upper end received in one of said openings, and an outwardly directed first flange located adjacent the reservoir when the first conduit means is connected to the reservoir;
   second elongated conduit means having an upper end received in the other of said openings, and an outwardly directed second flange located adjacent the reservoir when the second conduit means is connected to the reservoir; and clip means for releasable fastening the first and second flanges to the protuberance wherein the clip means has a first end, and a second end, and which comprises a first hook portion of the first end to receive at least one of the first and second conduit means adjacent the first and second flanges defining the first end of the clip means, a second hook portion at the second end to receive the protuberance defining the second end of the clip means, and a central portion connecting the first and second hook portions.

4. The device of claim 3 wherein the second hook portion extends partially around the protuberance.

5. A retaining device, comprising:

a reservoir for retaining a liquid having a wall defining openings;

a humidifier;

first elongated conduit means having an upper end and an lower end;

second separate elongated conduit means having an upper end and a lower end, the upper ends of the first and second conduit means being removably connected to the openings of the reservoir;

means for connecting a lower end of the first and second conduit means in fluid communication to the humidifier; and means for retaining the upper ends of both the first and second conduit means to the reservoir to prevent them from inadvertant removal from the reservoir, wherein the upper ends of the first and second conduit means have an outwardly directed flange, wherein the reservoir has an outwardly directed protuberance spaced from the openings, and in which the retaining means comprises means for clipping the flanges to the protuberance.

6. The device of claim 5 further comprising a pair of hollow spikes at an upper end of the first and second conduit means, respectively, and removably received through the openings of the wall of the reservoir, said spikes being in fluid communication with the respective conduit means and the reservoir.

7. A retaining device, comprising:

a reservoir for retaining a liquid and having a pair of lower openings and an outwardly directed protuberance adjacent the openings;

first elongated conduit means having an upper end received in one of said openings, and an outwardly directed first flange located adjacent the reservoir when the first conduit means is connected to the reservoir;

second separate elongated conduit means having an upper end received in the other of said openings, and an outwardly directed second flange located adjacent the reservoir when the second conduit means is connected to the reservoir; and clip means for releasable fastening the first and second flanges to the protuberance wherein the clip means has a first end, and a second end, and which comprises a first hook portion at the first end to receive at least one of the first and second conduit means adjacent the first and second flanges such that the first hook portion retains the first and second flanges adjacent the reservoir, a second hook portion at the second end to receive the protuberance, and a central portion connecting the first and second hook portions.

8. The device of claim 7 wherein the second hook portion extends partially around the protuberance.

9. A retaining device, comprising:

a reservoir for retaining a liquid and having a pair of lower openings and a lower outwardly directed protuberance adjacent the openings, with the openings located on a side of the reservoir spaced from the protuberance and with the openings being generally aligned with the protuberance;

first elongated conduit means having an upper end received in one of said openings, and a outwardly directed first flange located adjacent the reservoir when the first conduit means is connected to the reservoir;

second separate elongated conduit means having an upper end received in the other of said openings, and an outwardly directed second flange located adjacent the reservoir when the second conduit means is connected to the reservoir such that the first and second conduit means extend from a side wall of the reservoir and are generally aligned relative to the protuberance; and clip means for releasable fastening the first and second flanges to the protuberance wherein the clip means has a first end, and a second end, and which comprises a first hook portion at the first end to receive at least one of the first and second conduit means adjacent the first and second flanges, such that the first hook portion retains the first and second flanges adjacent the reservoir, a second hook portion at the second end to receive the protuberance, and a central portion connecting the first and second portions, with said central portion being formed at an angle between said first and second hook portions, such that the central portion extends along a lower wall of the reservoir towards the protuberance and along said side wall towards the first and second conduit means, with the distance between the first and second hook portions being such that the first hook portion snugly engages said one conduit means and the second hook portion snugly engages the protuberance.

10. The device of claim 9 wherein the second hook portion extends partially around the protuberance.

11. A retaining device comprising:

a reservoir for retaining a liquid and having a pair of lower openings and an outwardly directed protuberance spaced from the openings;

first elongated conduit means having an upper end received in one of said openings, and an outwardly directed first flange located adjacent the reservoir when the first conduit means is connected to the reservoir;

second separate elongated conduit means having an upper end received in the other of said openings, and an outwardly directed second flange located adjacent the reservoir when the second conduit means is connected to the reservoir such that the first and second conduit means are spaced form the protuberance; and clip means for releasable fastening the first and second flanges to the protuberance wherein the clip means had a first end, and a second end, and which comprises a first hook portion at the first end to receive at least one of the first and second conduit means adjacent the first and second flanges, such that the first hook portion extends along the first and second flanges and retains the first and second flanges adjacent the reservoir, a second hook portion at the second end to receive the protuberance, and a central portion connecting the first and second hook portions, with the distance between the first and second hook portions being such that the first hook portion snugly engages the said one conduit means and the second hook portion snugly engages the protuberance.

12. The device of claim 11 wherein the second hook portion extends partially around the protuberance.

* * * * *